(12) United States Patent
Liniger et al.

(10) Patent No.: US 7,771,393 B2
(45) Date of Patent: Aug. 10, 2010

(54) INSERTION DEVICE FOR AN INSERTION HEAD, IN PARTICULAR FOR AN INFUSION SET

(75) Inventors: Jurg Liniger, Ostermundigen (CH); Pascal Rutti, Neuendorf (CH); James Collins, Cambridgeshire (GB)

(73) Assignee: Roche Diagnostics International AG, Steinhausen (CH)

( * ) Notice: Subject to any disclaimer, the term of this patent is extended or adjusted under 35 U.S.C. 154(b) by 127 days.

(21) Appl. No.: 12/047,551

(22) Filed: Mar. 13, 2008

(65) Prior Publication Data

US 2008/0249472 A1 Oct. 9, 2008

(30) Foreign Application Priority Data

Mar. 14, 2007 (EP) ................... 07005215

(51) Int. Cl.
*A61M 5/20* (2006.01)
(52) U.S. Cl. .................................... 604/157
(58) Field of Classification Search ................ 604/157, 604/164.08, 164.12, 890.1
See application file for complete search history.

(56) References Cited

U.S. PATENT DOCUMENTS

| | | | | |
|---|---|---|---|---|
| 4,968,303 | A | * 11/1990 | Clarke et al. | ................. 604/187 |
| 5,637,094 | A | * 6/1997 | Stewart et al. | ............... 604/135 |
| 5,848,990 | A | 12/1998 | Cirelli et al. | |
| 6,607,509 | B2 | 8/2003 | Bobroff et al. | |
| 2003/0125669 | A1 | 7/2003 | Safabash et al. | |
| 2003/0199823 | A1 | 10/2003 | Bobroff et al. | |
| 2005/0035014 | A1 | 2/2005 | Cane | |

FOREIGN PATENT DOCUMENTS

| | | | |
|---|---|---|---|
| DE | 19821723 | C1 | 11/1999 |
| DE | 20320207 | U1 | 11/2004 |
| DE | 202004017862 | | * 3/2005 |
| DE | 102004039408 | A1 | 3/2006 |
| EP | 1652547 | A1 | 5/2006 |
| EP | 1764125 | A1 | 3/2007 |

(Continued)

OTHER PUBLICATIONS

European Search Report for 07 005 215.

(Continued)

*Primary Examiner*—Nicholas D Lucchesi
*Assistant Examiner*—Brooke M Matney
(74) *Attorney, Agent, or Firm*—Dorsey & Whitney LLP

(57) ABSTRACT

An insertion device for an infusion set, the insertion device including a two-part housing and a retainer or a retention means by which the infusion set can be temporarily held on the device, and a driver or a drive means including a pretensionable spring for providing the drive energy for an insertion movement of the infusion set, wherein one of the housing parts can be pivoted relative to the other to engage the infusion set and, after engagement of the infusion set, they can be pivoted again, as a result of which the spring is pretensioned and the insertion device is brought to a ready-to-use state. After the insertion movement has been triggered, the infusion set is separated from the device, such that it can execute the greatest part of the insertion movement free of the retainer.

40 Claims, 7 Drawing Sheets

FOREIGN PATENT DOCUMENTS

| | | | |
|---|---|---|---|
| FR | 2725902 | A1 | 4/1996 |
| WO | 2004101071 | A2 | 11/2004 |
| WO | 2004110527 | A1 | 12/2004 |
| WO | 2005037184 | A1 | 4/2005 |
| WO | 2005065748 | A1 | 7/2005 |
| WO | 2006015507 | A2 | 2/2006 |
| WO | 2006108185 | A1 | 10/2006 |
| WO | 20060129196 | A1 | 12/2006 |

OTHER PUBLICATIONS

European Search Report for 07 005 216.
European Search Report for 07 005 217.

\* cited by examiner

INSERTION DEVICE FOR AN INSERTION HEAD, IN PARTICULAR FOR AN INFUSION SET

CROSS REFERENCE TO RELATED APPLICATIONS

This application claims priority to European Application No. 07 005 215.4, filed on Mar. 14, 2007, the contents of which are hereby incorporated in their entirety by reference herein.

BACKGROUND

The present invention relates to devices for injecting, infusing, administering, delivering or dispensing a substance, and to methods of making and using such devices. More particularly, it relates to an insertion device for an insertion head, an arrangement comprising the insertion device and an insertion head that is or can be received in the latter, a use of the insertion device or of the arrangement, and a method for applying an insertion head.

In patients with a regular requirement for a medicament that can be administered by direct delivery into the body tissue or into the blood stream, for example certain groups of patients suffering from pain, or patients with type I and type II diabetes, it can be useful to supply the body with the required quantity of medicament in liquid form via a cannula that is introduced at a suitable location into the body and that remains there over quite a long period of time. For this purpose, a cannula arrangement, designated as an infusion set or port, depending on its design, is secured on the patient's skin, in such a way that the cannula passes through the skin and into the body.

Efforts are also increasingly being made to monitor certain medical parameters of a patient, for example the blood sugar value, continuously over quite a long period of time. For this purpose, a sensor arrangement, for example, is placed on the patient's body and, with a puncturing tip of a suitable sensor, passes through the skin and into the patient's body.

To avoid infections, the infusion set, the port or the sensor arrangement has to be changed at regular intervals, for example every three days. In outpatient treatment, for example in the case of diabetics, this is often done by the patients themselves and, on account of the introduction of the infusion cannula or of the puncturing tip into the skin, is associated with a certain amount of pain. It is therefore important that such infusion sets, ports or sensor arrangements can be applied easily and safely, which is why many manufacturers have in the meantime started designing their products as insertion heads for special insertion devices with the aid of which these insertion heads can be applied to the patient's body. Application is made easier in this way, and the pain occasioned by the application is reduced to a minimum, thanks to the quick and targeted puncturing procedure.

Thus, for example, U.S. Pat. No. 6,607,509 B2 discloses insertion devices for infusion sets, in which the infusion set is placed abruptly onto the application site by the force of a pretensioned spring, and the cannula penetrates into the tissue of the patient. After application of the infusion set, the insertion device has to be uncoupled and removed from the infusion set, which has the disadvantage that this may cause irritation at the puncture site by force exerted on the inserted cannula.

WO 2004/110527 A1 discloses, in addition to insertion devices as described above, also similar insertion devices for infusion sets in which, however, the infusion set is already automatically separated from the insertion device upon insertion into the body of the patient. Compared to the previously described insertion devices, this arrangement affords the advantage that only small friction losses occur within the insertion device, such that an abrupt application is made possible with a correspondingly short pain interval and, in addition, irritation at the puncture site, caused by subsequent detachment of the insertion device from the insertion head, is avoided. However, said insertion devices have the disadvantage of being relatively complicated to use and of requiring lots of operating steps.

SUMMARY

An object of the present invention is therefore to make available an insertion device, an arrangement comprising an insertion device with an associated insertion head, and a method for applying an insertion head, all of which do not have, or at least partially avoid, the disadvantages of the prior art.

In one embodiment, the present invention comprises an insertion device for an infusion set, the insertion device comprising a two-part housing, a retainer by which the infusion set can be temporarily held on the device, and a driver including a pretensionable spring for providing the drive energy for an insertion movement of the infusion set, wherein one of the housing parts can be pivoted relative to the other to engage the infusion set and, after engagement of the infusion set, can be pivoted again, as a result of which the spring is pretensioned and the insertion device is brought to a ready-to-use state. After the insertion movement has been triggered, the infusion set moves through at least part of the insertion movement free of the retainer.

In one embodiment, the present invention comprises an insertion device for an infusion set, the insertion device including a two-part housing and a retainer or retention means by which the infusion set can be temporarily held on the device, and a driver or a drive means including a pretensionable spring for providing the drive energy for an insertion movement of the infusion set. To allow the infusion set to be engaged in the retention means, one of the housing parts can be pivoted relative to the other. After engagement of the infusion set, they can be pivoted together again, as a result of which the spring is pretensioned and the insertion device is brought to a ready-to-use state. After an insertion movement has been triggered, the infusion set is separated from the retention means, such that it can execute the greatest part of the insertion movement free of the retention means.

Accordingly, a first aspect of the present invention concerns an insertion device for an insertion head with at least one infusion cannula and/or at least one puncturing tip. An insertion head to be applied with the insertion device can therefore comprise, for example, a single infusion cannula or a single puncturing tip, several cannulas or several puncturing tips, or one or more cannulas and one or more puncturing tips and, furthermore, can be designed, for example, as an infusion set, as a port and/or as a sensor arrangement, for example for measuring the blood sugar value. In some embodiments, the insertion device has a housing having one or more contact faces, with which the insertion device is placed onto the skin of the patient for application of the insertion head. The insertion device also comprises a retainer or retention means, for example two mutually opposite leaf spring elements or spring shackles, with which the insertion head to be applied can be temporarily held on the insertion device, with the result that, during the actual application of the insertion head, only the insertion device has to be held by the user on the application site. The insertion device also comprises drive means, with which the insertion head to be applied can be moved, relative to the contact face in the longitudinal direction of one of the infusion cannulas or puncturing tips, from a first position, in which the insertion head is held by the retention means in such a way that all its infusion cannulas and puncturing tips are set back relative to the contact face or faces, for avoiding inadvertent contact with the user, to a second position, in which all its infusion cannulas and puncturing tips protrude substantially completely beyond the contact face, to permit introduction of these infusion cannulas and puncturing tips into the body of the patient when the insertion device is placed with the contact face on the skin of the patient. This movement of the insertion head, by which the insertion head is actually applied to the body, may be referred to or thought of as an insertion movement.

In some embodiments, the housing has a first housing part and a second housing part, the first housing part carrying the retention means and the contact face or, if there are several contact faces, some of the contact faces. The second housing part is movable relative to the first housing part, e.g. from a first, basic position, in which the two housing parts are positioned relative to one another such as is the case on application of the insertion head to the body of the patient and in which it is typically difficult or impossible to engage the insertion head to be applied into the retention means, to a loading position, in which the retention means are accessible, e.g., much more accessible than in the first position, for correct engagement of the insertion head that is to be applied. After the insertion head has been engaged into the retention means, the second housing part can be moved back to the first, basic position. The insertion device is designed in such a way that, after the insertion head has been engaged into or with the retention means and the second housing part has been moved back to the basic position, the insertion head is held ready for application in the first position by the retention means, i.e. in the state ready for introduction into the skin. In the case of insertion heads with deployable cannulas or puncturing tips, "ready for application" means that the cannula or puncturing tip is completely deployed and, if provided for, also locked in this position. Moreover, the insertion device is designed in such a way that the insertion head is separated from the retention means at the start of the insertion movement, such that it can execute the greatest part of the insertion movement free of the retention means, i.e. in "free flight" or, at any rate, guided by lateral guides, and, after application, there is no longer any connection between the insertion head and the insertion device, with the result that the insertion device can be removed from the insertion head applied to the body, without any danger of irritation of the application site.

The present invention permits the provision of insertion devices for insertion heads which have a very short insertion phase with a correspondingly short pain interval, avoid irritation of the puncture site upon release of the insertion head from the insertion device, and at the same time are much easier to use than the insertion devices of this type known today.

In a preferred embodiment, the retention means is designed in such a way that the insertion head can be held in the first position purely with a force fit, e.g. by clamping between two spring clips, purely with a form fit, or with a combination of a force fit and form fit. In particular, in the case of a purely force fit, the advantage is that the insertion head, at the start of the insertion movement, can be easily knocked out of the retention means by a thrust element of the drive means and is thus released from said retention means.

In some preferred embodiments, the insertion head in accordance with the present invention can be held in the loading position by the retention means purely with a form fit or with a combination of a force fit and form fit, and, in some preferred embodiments, the form fit is cancelled during the movement of the second housing part from the loading position to the basic position.

Alternatively, in some preferred embodiments, the insertion device in accordance with the present invention is designed in such a way that the insertion head can be held in the loading position by the retention means purely with a force fit, and the force fit is reduced during the movement of the second housing part from the loading position to the basic position. This can be achieved, for example, by the insertion head being held with a force fit by spring shackles whose free resilient length increases during the movement from the loading position to the basic position. However, alternative embodiments are also possible in which there is purely a force fit of equal strength both in the loading position and also in the basic position.

In the alternative embodiments in which a form fit is cancelled or a force fit is reduced during the movement from the loading position to the basic position, an advantage, especially when using insertion heads with a fixed infusion cannula or puncturing tip, is that the insertion head is held more firmly in the loading position than in the basic position, with the result that the needle guard or cannula guard can be removed without any danger of the insertion head coming loose again from the retention means.

In another preferred embodiment, the insertion device in accordance with the present invention is designed in such a way that, at least during a large part of the insertion movement or during the entire insertion movement of the insertion head, the retention means remain unmoved relative to the contact face. It may be preferred that the retention means is designed to be immovable relative to the contact face or some of the contact faces carried by the first housing part.

In yet another preferred embodiment, the drive means or powering mechanism of an insertion device in accordance with the present invention comprises one or more energy-storing elements for providing the drive energy for the insertion movement, for example helical springs, leg springs or leaf springs made of metal or plastic, pneumatic compression springs or rubber spring elements. This gives the advantage that the insertion device can be used at any time and in any place, independently of external sources of energy, and can also be produced inexpensively.

In some preferred embodiments, the energy-storing element can be pretensioned either by the movement of the second housing part from the basic position to the loading position or by the movement of the second housing part from the loading position to the basic position, or by both movements of the second housing part. The advantage of the first variant is that the force for moving the second housing part back to the basic position can be relatively low, which, when using insertion heads with fixed infusion cannulas or puncturing tips, reduces the risk of the user being injured by an uncontrolled movement with the insertion head engaged. It is also advantageous that the movement that requires the greatest force, at least in embodiments with second housing parts that are pivotable and that can be displaced transverse to the direction of the insertion movement, can take place in the pulling direction of the movement, which, compared to a movement in the pushing direction, promotes controlled handling of the insertion device. The second variant meanwhile has the advantage that pressing structural elements together is often felt to be easier than pulling them apart, such that, depending on the design involved, this variant may facilitate operation of the insertion device according to the invention. The third variant, by contrast, has the advantage that the double movement is available for pretensioning the energy-storing element, with the result that the force needed for this may be much less, which similarly contributes to controlled operation. All of these variants additionally have the advantage that they permit the provision of inexpensive and purely mechanical insertion devices, which are ready to be used at any time without external energy. This is in contrast to other preferred embodiments of the insertion device according to the present invention in which the pretensioning of the energy-storing element is obtained by electrical elements, for example electric motors. In such embodiments, switches and/or sensors that control the electrical elements for pretensioning the energy-storing elements may be present.

In some preferred embodiments, the insertion device is designed in such a way that, with the insertion head located in the first position, the energy-storing element can be made ready in the pretensioned state, and the insertion movement can then be triggered by actuation of one actuation member, or by simultaneous or sequential actuation of several actuation members, with increasing relaxation of the energy-storing element.

Suitable actuation members can be of a purely mechanical construction, for example as trigger latches or trigger slides, or can, for example, also comprise electrical or electronic elements, for example an electrically activated latch that can be triggered via a switch and/or a sensor with evaluation electronics. The selected actuation member should help provide for a controlled application of the insertion head.

In the last-mentioned embodiments, it is also advantageous for the drive means to comprise a thrust element for transmitting the drive energy to the insertion head to be applied and be designed in such a way that, by displacing the thrust element counter to the direction of the insertion movement and subsequently locking it with a lock or locking means that can be released by the actuation members, the energy-storing element can be pretensioned and made ready in the pretensioned state. Such constructions can be produced inexpensively, function in a reliable manner and also permit a high initial acceleration and, consequently, a rapid insertion movement, thereby minimizing the pain that is occasioned by the application upon introduction of the infusion cannula or of the puncturing tip into the body.

In yet another preferred embodiment of the insertion device in accordance with the present invention, the second housing part, for the movement from the first, basic position to the loading position and back again, can be pivoted relative to the first housing part, which favors a simple structural design of the connection of the two housing parts to one another.

In an alternative preferred embodiment, the second housing part, for the movement from the basic position to the loading position and back again, can be displaced relative to the first housing part transverse or perpendicular to the direction of the insertion movement. Compared to the above-described embodiments, this provides for alternatives in respect of the structural design of the connection of the two housing parts.

In yet another preferred embodiment of the insertion device, the second housing part carries some of the contact faces. Accordingly, during the movement of the second housing part from the basic position to the loading position, these contact faces are temporarily separated from the other contact faces carried by the first housing part, thereby permitting embodiments in which the retention means is easily accessible in the loading position.

In yet another preferred embodiment, the retention means is designed in such a way that the insertion head can be engaged therewith or into them by being pushed in a direction transverse or perpendicular to the direction of the insertion movement. In this way, the risk of injury can be reduced, particularly when using insertion heads with fixed cannulas or puncturing tips.

In yet another preferred embodiment of the present invention, the insertion device has at least two actuation members, which have to be actuated simultaneously to trigger the insertion movement. A first of the actuation members is designed such that it can be actuated by the contact face of the insertion device being pressed onto the body of the patient, in some preferred embodiments by its being pressed on in the direction of the insertion movement, which is advantageous if the insertion is performed at an angle of approximately 90° to the surface of the body. This embodiment of the insertion device reduces the danger of inadvertent triggering of the insertion device when ready for application, and thus also reduces the chances of the user sustaining an injury.

In some preferred embodiments, the first actuation member is designed as a slide-shaped or button-shaped element, and at the same time forms the contact face or, if there are several contact faces, forms all the contact faces of the insertion device. The advantage of this is that the first actuation member can be safely actuated independently of the surface contour of the application site on the patient's body.

As an alternative to purely mechanical embodiments of the first actuation member, it may be preferable to provide electrical first actuation members. This is possible, for example, in the form of an electrical latch element which is controlled by one or more skin contact sensors (e.g. conductivity sensors) arranged on the contact face and by associated control electronics, in such a way that it is activated when the insertion device is placed correctly onto the application site.

In embodiments of the present invention comprising at least two actuation members, it may be preferred if at least one of the actuation members, e.g. the second actuation member, is designed as a button-shaped element which can be actuated when a user presses it with a finger tip. The actuation direction may be transverse or perpendicular to the direction in which the insertion device is pressed onto the body of the patient, which direction is the same as the direction of the claimed insertion movement and, consequently, the direction of introduction of the infusion cannula or puncturing tip into the skin. This second actuation member can be of a purely mechanical construction, for example as trigger latch or trigger slide, or can, for example, also comprise electrical or electronic elements, for example an electrically activated latch that can be triggered via a switch and/or a sensor with evaluation electronics. By this embodiment, it is possible to further reduce the danger of inadvertent actuation of this actuation member together with the claimed first actuation member, such that the danger of inadvertent triggering of the insertion device is lessened still further.

In some embodiments of the present invention, it may also be advantageous if the direction of actuation is parallel or substantially parallel to the direction of pressing-on.

In yet another preferred embodiment of the insertion device according to the present invention with at least two actuation members, its actuation members, which are to be actuated to trigger the insertion movement, are coupled to one another in such a way that, by actuating one of these actuation members, a blocking or locking of another actuation member or of several other actuation members can be cancelled. In this way, the construction can be simplified, since only a single trigger mechanism is necessary. For example, if one actuation member with electrical elements is present, a simple and inexpensive structure can be produced, for example by an electrical latch element that can only be triggered when two switches or sensors are actuated simultaneously or a combination of at least one switch and at least one sensor.

In yet another preferred embodiment of an insertion device with one or at least two actuation members, all the actuation members, which have to be actuated simultaneously to trigger the insertion movement, are designed in such a way that they can be actuated with one hand by the user. Accordingly, one-handed operation of the insertion device is possible, as a result of which the insertion head can be applied by the patient even in areas of the body that are inaccessible with both hands or are difficult to access with both hands, for example in the area of the hips.

In yet another preferred embodiment of the insertion device with one or more actuation members, the actuation members, which have to be actuated simultaneously to trigger the insertion movement, are designed in such a way that, when an actuating force ceases, they automatically readopt their unactuated state. This further increases the degree of safety against inadvertent triggering of the insertion device.

In another preferred embodiment of the present invention, the insertion device has means for effecting a displacement, e.g. a transverse displacement, of a displaceable actuation member of an insertion head to be held in the retention means, with one or several deployable infusion cannulas and/or one or several deployable puncturing tips, during the movement of the second housing part from a loading position to a basic position, so as to permit automatic deployment of all the deployable infusion cannulas and all the deployable puncturing tips of the insertion head during the movement of the second housing part from the loading position to the basic position. In this way, it is possible for insertion heads adapted to the insertion device and with deployable infusion cannulas or puncturing tips to be fitted in the protected state, i.e. with the cannulas or puncturing tips folded inwardly, in the loading position into the retention means of the insertion device, and for the cannulas or puncturing tips of the insertion head to be then automatically deployed by moving the second housing part into the basic position, as a result of which the insertion head is brought into the state ready for application. In this way, the danger of the user being injured by the cannulas or the puncturing tips, when preparing for the application of the insertion head, can be reduced and/or practically eliminated.

In the embodiment described above, it is preferable if the means for effecting a displacement of a displaceable actuation member comprise a run-on surface which is formed by the second housing part and by which an actuation member, displaceable transverse to the direction of the insertion movement, of a correspondingly designed insertion head to be held in the retention means with deployable infusion cannula or puncturing tip, can be displaced during the movement of the second housing part from the loading position to the basic position, to permit automatic deployment of the deployable infusion cannulas and puncturing tips of the insertion head during the movement of the second housing part from the loading position to the basic position. Such means for effecting displacement of a displaceable actuation member can be readily made available in a simple and inexpensive way.

In some preferred embodiments, the means for effecting a displacement of a displaceable actuation member comprise a lever mechanism with which an actuation member, which is displaceable transverse to the direction of the insertion movement, of a correspondingly designed insertion head to be held in the retention means and with deployable infusion cannula or puncturing tip during the movement of the second housing part from the loading position to the basic position, to permit automatic deployment of the deployable infusion cannulas and puncturing tips of the insertion head during the movement of the second housing part from the loading position to the basic position. This permits considerable freedom in terms of the structural configuration both of the insertion device and also of the associated insertion head.

It is also advantageous if the insertion device is designed in such a way that it can be used several times to apply an insertion head. Costs can thereby be saved.

A second aspect of the present invention concerns an arrangement that comprises an insertion device according to the first aspect of the invention, and an insertion head which is or can be received in the latter and which, in some preferred embodiments, is designed as an infusion set, port and/or sensor arrangement and has at least one infusion cannula and/or at least one puncturing tip. The insertion head can therefore have, for example, a single infusion cannula or puncturing tip, several cannulas or puncturing tips, or one or more cannulas and one or more puncturing tips. By engaging a suitable matching insertion head into the insertion device according to the first aspect of the invention, such an arrangement is achieved. In addition to the marketing of reusable insertion devices according to the first aspect of the invention and of associated insertion heads, such as associated infusion sets, ports or sensor arrangements, which are joined together by the user shortly before use to form arrangements according to the invention, provision is also made for preassembled arrangements according to the invention to be offered as disposable articles, with the insertion device being disposed of after the insertion head has been applied.

In a preferred embodiment of the arrangement according to the present invention, the insertion head is an insertion head with at least one deployable infusion cannula and/or at least one puncturing tip, all the infusion cannulas and puncturing tips of the insertion head being folded inwardly in the unactuated state, in which the insertion head is intended to be received in the loading position in the retention means or is already received in the retention means, and the insertion device and the insertion head being designed in such a way that all the deployable infusion cannulas and puncturing tips of the insertion head are automatically deployed during the movement of the second housing part from the loading position to the basic position. As has already been mentioned in the discussion of the first aspect of the invention, this can reduce or practically rule out any danger of the user being injured by the cannula or puncturing tip when preparing to apply the insertion head.

A third aspect of the present invention concerns the use of the insertion device or of the arrangement according to one of the preceding aspects of the invention for applying an insertion head to the body of a patient, e.g. an insertion head designed as an infusion set, port and/or sensor arrangement and having at least one infusion cannula and/or at least one puncturing tip. Such uses are in accordance with the present invention and bring out clearly the advantages of the invention.

A fourth aspect of the present invention concerns a method for applying an insertion head to the body of a patient, e.g. an insertion head designed as an infusion set, port and/or sensor arrangement, using an insertion device according to the first aspect of the present invention.

In a first method step, the insertion device according to the present invention is made ready with the second housing part arranged in the loading position, in which an engagement of the insertion head into the retention means is not possible, or possible only with difficulty.

In another step, the second housing part is moved from the basic position to the loading position, as a result of which the retention means are made available for the engagement of the insertion head.

In a third step, the insertion head adapted to the insertion device, and with at least one infusion cannula and/or at least one puncturing tip, is engaged into the retention means, in such a way that it is held by the retention means. An inventive arrangement according to the second aspect of the invention is thus present in which the insertion head can have a single infusion cannula or puncturing tip, several cannulas or puncturing tips, or one or more cannulas and one or more puncturing tips.

In another step, the second housing part is moved back from the loading position to the basic position in which the insertion head, after reaching the basic position, is held ready for application by the retention means in the first position. The insertion device is now ready for the actual application process.

For this purpose, the insertion device, in a fifth step of the method according to the present invention, is arranged with the contact face or contact faces of the insertion device on the desired application site on the body of the patient in such a way that the infusion cannulas and puncturing tips of the insertion head can penetrate correctly into the body during the subsequent insertion movement.

In another step, the insertion movement of the insertion head is triggered, whereby the insertion head is separated from the retention means at the start of the insertion movement, in such a way that it executes at least the greatest part of the insertion movement free of the retention means.

The method of the present invention for applying an insertion head to the body of a patient using an insertion device permits a short insertion phase with a correspondingly short pain interval, and irritation of the puncture site upon release of the insertion head from the insertion device can be reliably avoided, and at the same time the method is easier to carry out compared to methods of this type known today.

In a preferred embodiment of the method, the insertion head is held in the first position by the retention means purely with a force fit, purely with a form fit, or with a combination of a force fit and form fit. In the case of a purely force fit, this affords the advantage that, at the start of the insertion movement, the insertion head can easily be knocked out of the retention means by a thrust element of the drive means and is thus detached from said retention means. In some embodiments, it may be preferred in this connection if, after being engaged into the retention means, the insertion head is held in the loading position by the retention means with a purely form fit or with a combination of a force fit and form fit. The form fit may be cancelled during the movement of the second housing part from the loading position to the basic position.

Alternatively, it may be preferred that, after it has been engaged into the retention means, the insertion head is held in the loading position by the retention means purely with a force fit, and the force fit is reduced during the movement of the second housing part from the loading position to the basic position. Embodiments are also provided, however, in which the insertion head is held by the retention means purely with a force fit both in the loading position and also in the basic position, in each case with a force fit of the same strength.

In method variants of the present invention in which a form fit is cancelled or, respectively, a force fit is reduced during the movement from the loading position to the basic position, one advantage, e.g. when using insertion heads with fixed infusion cannulas or puncturing tips, is that the insertion head is held more firmly in the loading position than in the basic position, with the result that the needle guard or cannula guard can be removed without any danger of the insertion head coming loose again from the retention means.

In yet another preferred embodiment of the method in accordance with the present invention, use is made of an insertion device whose drive means comprise at least one pretensionable energy-storing element for providing the drive energy for the insertion movement, the energy-storing element being pretensioned by the movement of the second housing part from the basic position to the loading position and/or by the movement of the second housing part from the loading position to the basic position. The individual method variants have various advantages, which have already been explained in the discussion of the corresponding embodiments of the first aspect of the present invention. All the variants also have the advantage that they favor the use of inexpensive, purely mechanical insertion devices, which are ready to use at any time without external energy. This is in contrast to the similarly proposed use of insertion devices in which the energy-storing element is pretensioned by electrical elements, for example electric motors.

In another preferred embodiment of a method in accordance with the present invention, the second housing part, in the movement from the basic position to the loading position and vice versa, is pivoted relative to the first housing part, which arrangement permits the use of simple and robust insertion devices according to the invention.

In yet another preferred embodiment of the method, the insertion head in the first position is held in the retention means with a force fit, the retention means being held immovable relative to the contact face during the insertion movement of the insertion head, which is achieved by their being designed immovably relative to the contact face or contact faces provided by the first housing part. This permits the use of structurally simple and correspondingly inexpensive and robust insertion devices according to the invention.

In yet another preferred embodiment of the method, use is made of an insertion device, the drive means of which have at least one pretensionable energy-storing element for providing the drive energy for the insertion movement, the energy-storing element being made ready in the pretensioned state, and the insertion movement then being triggered by actuation of an actuation member or by simultaneous or sequential actuation of several actuation members. This favors a controlled application process.

In some embodiments, it may be preferred that arranging the insertion device on the body of the patient and triggering the insertion movement is done with one hand, such that areas that are difficult to reach or can be reached with only one hand are also accessible for the application.

In yet another preferred embodiment of the method according to the present invention, an insertion head with at least one deployable infusion cannula and/or at least one deployable puncturing tip, and in a state in which all the deployable infusion cannulas and puncturing tips of the insertion head are folded inwardly, is engaged into the retention means. All the deployable infusion cannulas and puncturing tips of the insertion head are then deployed during the movement of the second housing part from the loading position to the basic position. The insertion head is then ready for application. In this way, the danger of the user sustaining an injury when preparing for the application can be reduced or practically eliminated.

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making the invention and/or its components may be selected from appropriate materials such as metal, metallic alloys, ceramics, plastics, etc.

Figure 1:
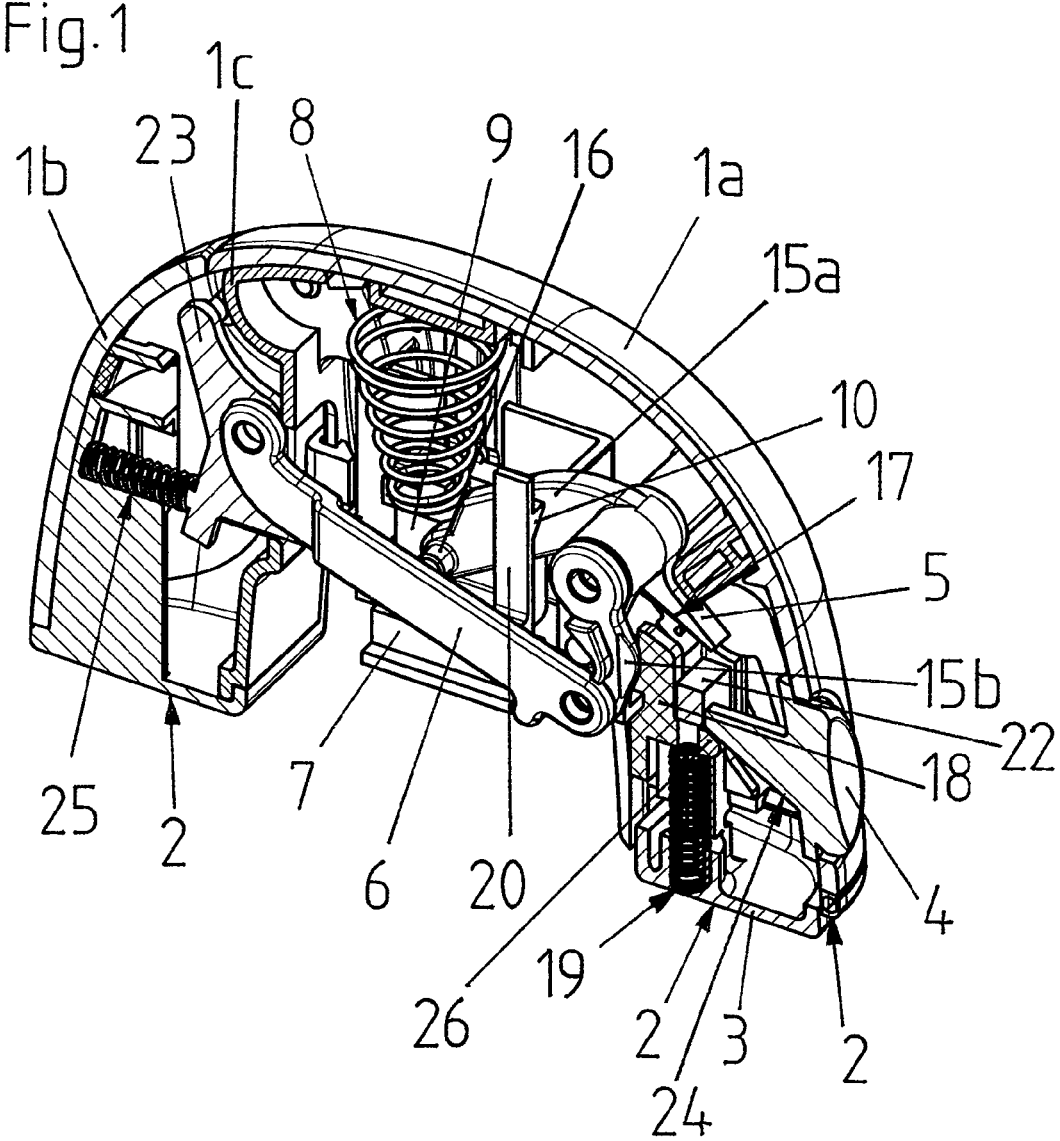
FIG. 1 is a vertical section through one embodiment of an insertion device according to the present invention, in the non-pretensioned basic state and without an insertion head.

An insertion device according to the present invention, for insertion heads with deployable infusion cannula, is shown in vertical section in FIG. 1, in the non-pretensioned state and without an insertion head. As can be seen here, the insertion device has a portal-like housing 1a, 1b which, on its underside, has contact faces 2 via which the insertion device is placed and pressed onto the body of a patient for application of an insertion head, e.g. of an infusion set, using the insertion device. One of the contact faces 2 is formed by a securing button 3, which protrudes downwards from the underside of the housing and which, to release the insertion device, when the latter is in a state ready for application by being placed and pressed onto the body of the patient, can be displaced into a release position in which the contact face 2 of the securing button 3 is essentially flush with that surface of the contact face 2 of the housing adjoining the securing button 3.

The insertion device also has a trigger knob 4 with which the insertion movement for applying the insertion head to the body of the patient can be triggered when the insertion device is in a state ready for application and the securing button 3 is arranged in the release position. The securing button 3 and trigger knob 4 thus represent two claimed actuation members 3, 4, which have to be actuated simultaneously in order to trigger the insertion movement.

Figure 2:
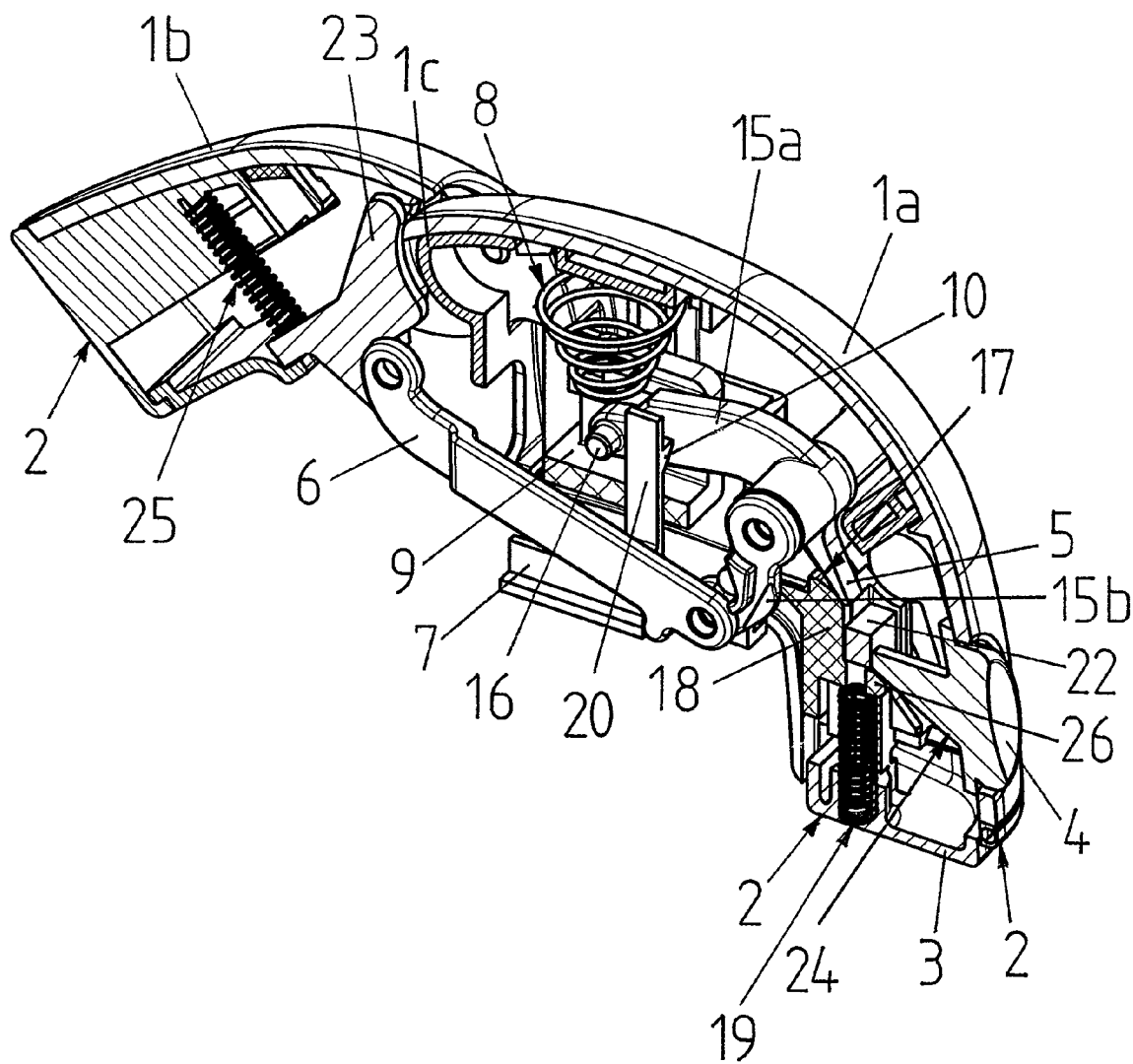
FIG. 2 is a vertical section through the insertion device of FIG. 1, during pretensioning.
Figure 3:
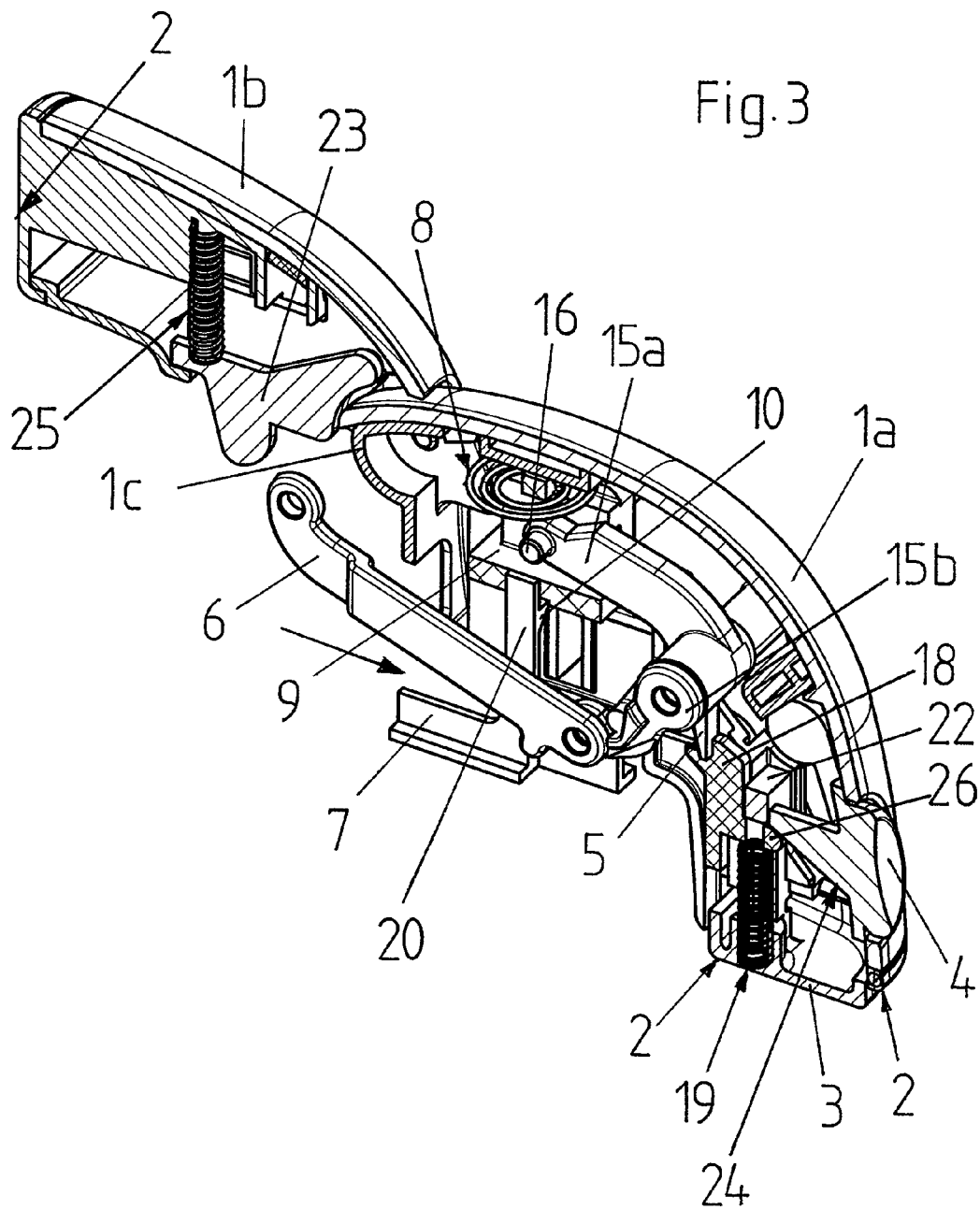
FIG. 3 is a vertical section through the insertion device of FIG. 1 at the end of the pretensioning operation.

As can be seen from a comparison with FIGS. 2 and 3, which show the insertion device during the pretensioning (FIG. 2) and at the end of the pretensioning procedure (FIG. 3), the housing comprises a first housing part 1a in which an inner housing part 1c connected fixedly thereto is arranged which has, as the claimed retention means, two mutually opposite retention elements like spring shackles (not visible) for force-fit engagement of an insertion head to be applied with the insertion device, and a second housing part 1b that can be pivoted relative to the first housing part 1a from the basic position shown in FIG. 1 to the loading position shown in FIG. 3.

As can also be seen, the insertion device comprises, as drive means, a helical spring 8 which acts on a hammer element 9. Helical spring 8 and hammer element 9 are arranged inside the first housing part 1a.

The hammer element 9 is connected to the second housing part 1b via a trigger lever 15, designed as a double lever (as at arms 15a and 15b) and mounted pivotably in the first housing part 1a, and via a pulling bracket 6, in such a way that, when the second housing part 1b pivots outwards, the hammer element 9 is moved upwards counter to the force of the helical spring 8 in the first housing part 1a, with increasing pretensioning of the helical spring 8. For this purpose, the trigger lever has, at its end towards the hammer element, two guide cylinders 16 (only one is shown) which, in a manner comparable to a sliding block, are guided in mutually opposite horizontal oblong holes (not shown) in the hammer element 9. The other end of the trigger lever 15 is connected to one end of the pulling bracket 6, the other end of which is in turn connected to the second housing part 1b, but in an area cut away for the cross-sectional view, for which reason this connection cannot be seen in the figures.

As can also be seen, the trigger lever has a catch projection 5 having a run-up ramp 17 with which, with its pivot movement which effects the increasing pretensioning of the spring 8, it moves a latch element 18 downwards counter to the force of a locking spring 19 until the catch projection 5 extends past the latch element 18 and then is locked in the situation shown in FIG. 3 by the latch element 18 shooting back under the force of the locking spring 19.

On reaching the upper position of maximum pretensioning shown in FIG. 3, the hammer element 9 engages with a catch lug 10 formed on a spring arm 20 of a slide 7 that is horizontally displaceable in the first housing part 1a counter to the force of a restoring spring (not shown), with the result that triggering of the hammer element 9 is already made impossible by this catch lug 10 alone. In this state, in which the second housing part 1b is pivoted to the maximum extent relative to the first housing part 1a, and which corresponds to the claimed loading state, a suitable insertion head 12 can now be pushed between the retention elements, in the direction indicated by an arrow in FIG. 3, and can thus be held on these, as is shown in FIG. 4.

Figure 4:
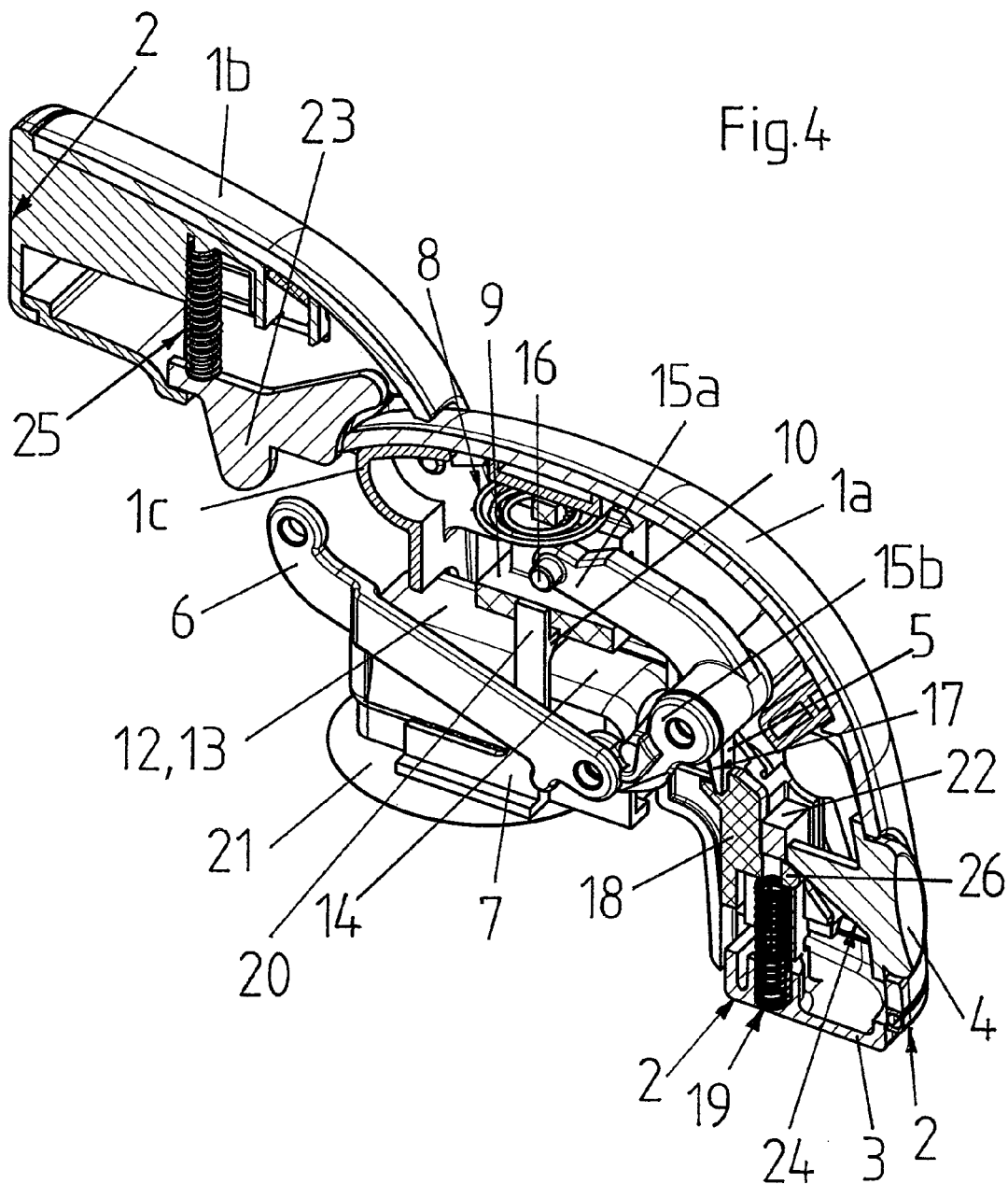
FIG. 4 is a view of the insertion device of FIG. 3, but with an insertion head arranged therein.

To bring the insertion device to a state ready for application or use, the second housing part now has to be pivoted from the loading position shown in FIG. 4 back to the basic position, which is possible despite the trigger lever being locked, because the arm 15b of the trigger lever connected to the pulling bracket 6 is connected so as to rotate about a suitable rotation angle relative to the arm 15a connected to the hammer element 9 and the catch projection 5. In this pretensioned basic state, the second housing part 1b locks reversibly with the first housing 1a by means of catch means (not shown) in such a way that it can be moved in the opposite direction, and back into the loading position, only after overcoming a high initial resistance. Suitable catch means are known to a person skilled in the art and could be formed, for example, by a lug held on a spring tongue and engaging with a run-on bevel in an undercut such that the locked connection can be released again by deflection of the spring tongue under increased force, by the run-on bevel running onto an edge of the undercut. Alternatively, provision is also made for the lock or catch means to be designed such that the locking action can be undone again by actuation of associated unlocking means, for example by pressing of an unlocking button.

At the same time as the movement of the second housing part 1b pivoting back to the basic position, the cannula 11 of the insertion head 12 is deployed by an actuation lever 23 mounted counter to the force of a support spring 25 on the second housing part 1b being pivoted with the second housing part 1b towards the insertion head 12. Thus, the left-hand housing part 13 of the insertion head 12, which forms a displaceable actuation member of the insertion head 12, is moved or pushed horizontally into the retention elements and at the same time pushing via the right-hand housing part 14 thereof, which is supported in the first housing part 1a of the insertion device and thus deploys the cannula 11 via a mechanism (not shown) located in the interior of the insertion head. In the present case, the insertion head 12 is an infusion set for insulin, which, in the state shown here prior to application, has a flexible cannula (soft cannula) supported by a puncture needle that is to be removed following the application and bears a fastening plaster 21 on its underside. For the purposes of explaining the present invention, however, a distinction does not have to be made here between puncture needle and flexible cannula, for which reason both are together designated in this example as "cannula 11".

During its displacement, the left-hand housing part 13 of the insertion head 12 carries with it the displaceably mounted slide 7 that supports the spring arm 20 with the catch lug 10 formed thereon, and displaces it toward the right until the catch lug 10 is positioned laterally alongside the hammer element 9 and the latter is now held in the pretensioned position exclusively via the locked first arm 15a of the trigger lever counter to the force of the spring 8. This situation, in which the insertion device is ready for application, is shown in FIG. 5.

Figure 5:
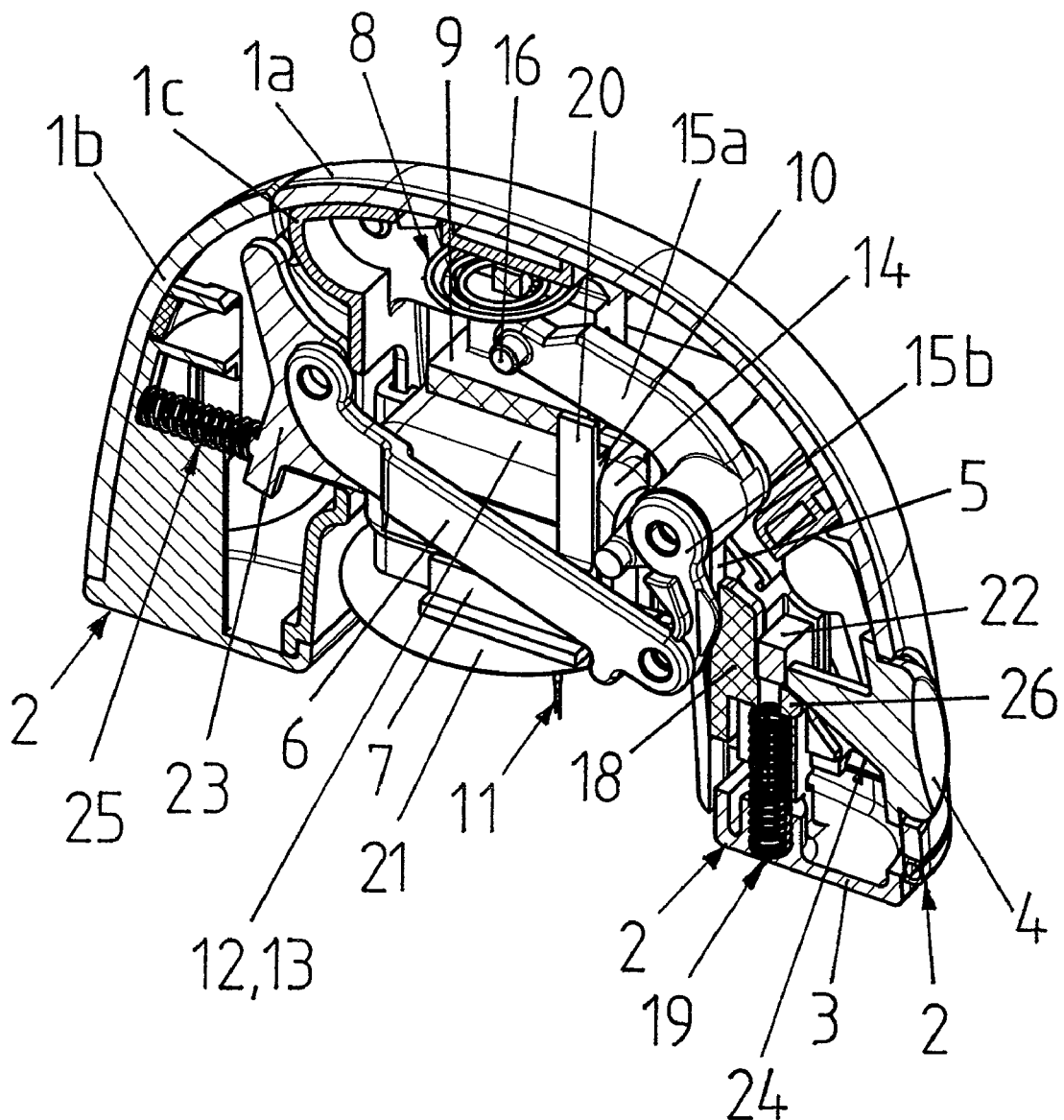
FIG. 5 is a vertical section through the secured insertion device ready for application.
Figure 6:
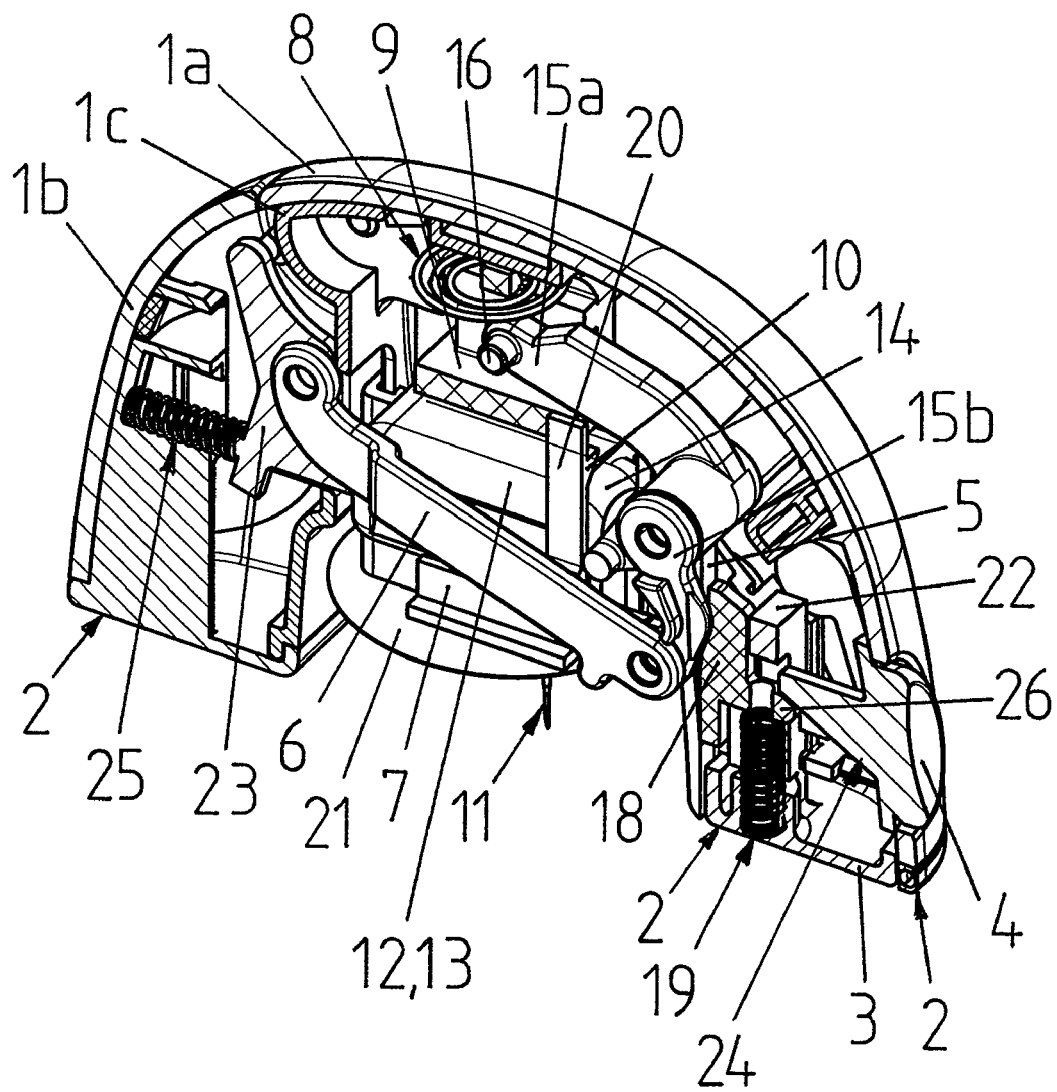
FIG. 6 is a view of the insertion device of FIG. 5, but in the released state.

As will be seen from a comparison of FIGS. 5 and 6, which show the insertion device in each case in the state ready for application, on the one hand in the secured state (FIG. 5) and on the other hand in the released state (FIG. 6), the securing button 3, on which the locking spring 19 bears via its end directed away from the latch element 18, forms a securing slide 22 in the first housing part 1a, which securing slide 22, in the situation shown in FIG. 5, has a form fit and prevents actuation of the trigger knob 4. Only when a pressure force is exerted on the securing button 3 counter to the direction of force of the locking spring 19, for example by pressing the insertion device onto the application site on the body of a patient, can it be pushed so far into the housing 1a that its underside, which bears a contact face 2, is essentially flush with the contact face 2 of the first housing part 1a adjoining it. In this position, which is shown in FIG. 6, the securing slide 22 frees the trigger knob 4.

Figure 7:
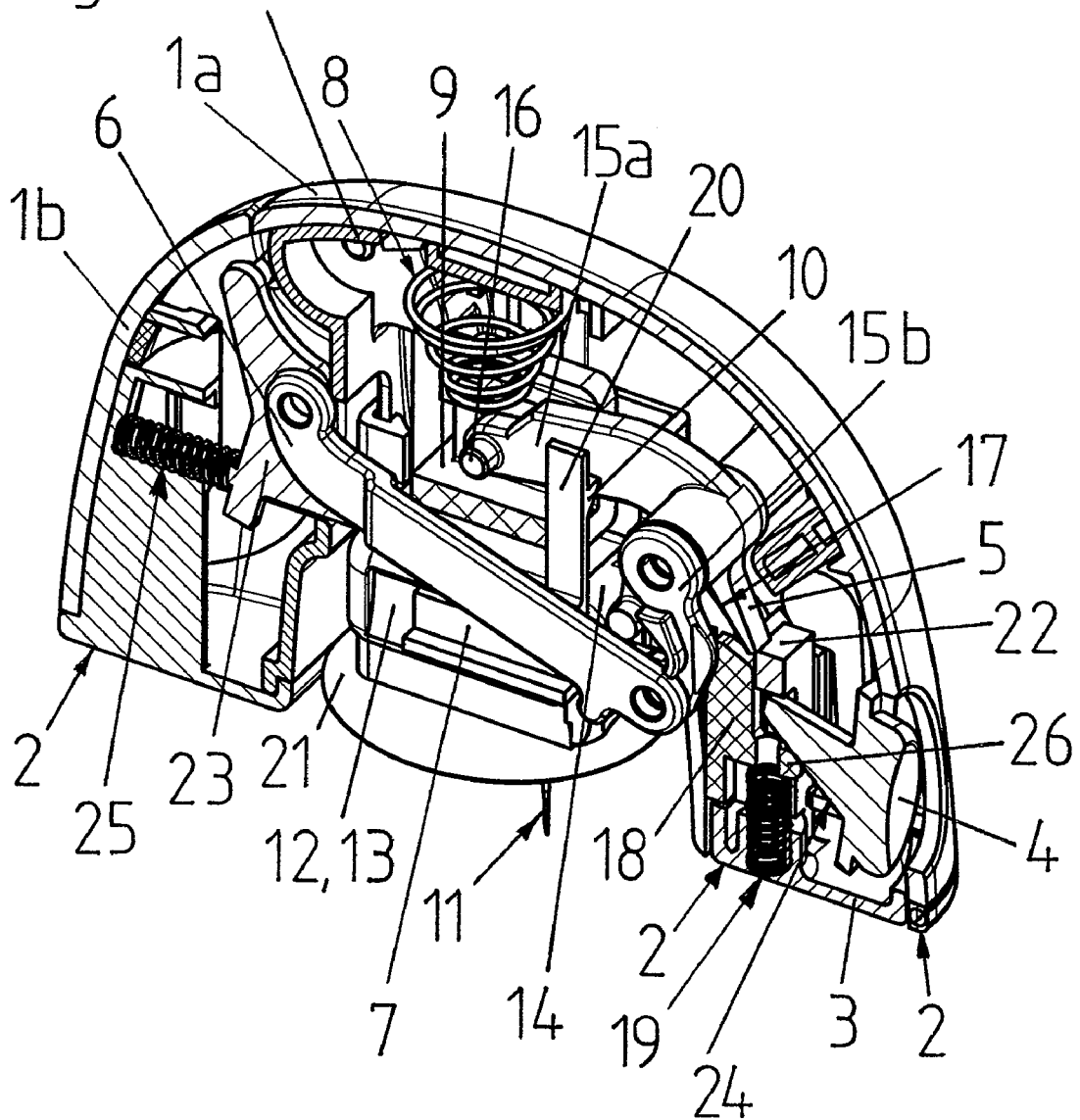
FIG. 7 is a view of the insertion device of FIG. 6, shortly after the trigger button is actuated.

As can be seen from FIG. 7, which shows the insertion device shortly after the trigger knob 4 is actuated, the trigger knob 4 has, on its face directed toward the interior of the housing 1a, a trigger ramp 24 which, upon actuation of the trigger knob 4, is moved along a control lug 26 of the latch element 18 and thus draws the latter downwards counter to the force of the locking spring 19, as a result of which the catch projection 5 of the trigger bar is freed and the hammer element 9 held at the first arm 15a thereof shoots downwards, driven by the force of the pretensioned helical spring 8. The hammer element 9 strikes the top face of the insertion head 12 held with a force fit in the claimed first position in the retention elements, releases the insertion head 12 from the retention elements and drives it down for application of the insertion head 12 to the body of the patient, with the cannula 11 penetrating into the body ahead of it, until the cannula 11 is completely inserted and the insertion head 12 lies with its underside on the surface of the body. The retention elements remain unmoved in the insertion direction relative to the housing 1a, 1b. The slide 7 then moves in the horizontal direction, driven by the force of the return spring, back to the position shown in FIGS. 1 to 3.

After the application, the applied insertion head 12 is completely separated from the insertion device, such that the latter can be removed without causing any irritation of the application site. It is then located back in the situation shown in FIG. 1 and can be used again for the application of an insertion head.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An insertion device for an infusion set, the insertion device comprising a two-part housing, a retainer which temporarily receives and holds the infusion set within the device, and a driver including a pretensionable spring for providing the drive energy for an insertion movement of the infusion set, wherein one of the housing parts can be moved relative to the other to engage the infusion set and, after engagement of the infusion set, can be moved again, as a result of which the spring is pretensioned and the insertion device is brought to a ready-to-use state, and wherein, after the insertion movement is initiated, the infusion set moves through at least part of the insertion movement free of the retainer.

2. An insertion device for an insertion head with at least one infusion cannula and/or at least one puncturing tip for introduction into the body of a patient, comprising:
   a) a housing having at least one contact face for placing the insertion device onto an application site on the body of the patient for application of the insertion head;
   b) a retention device which temporarily receives and holds the insertion head within the insertion device; and
   c) a drive for effecting an insertion movement of the insertion head relative to the contact face in the longitudinal direction of an infusion cannula or puncturing tip of the insertion head from a first position, in which the insertion head is held ready for application by the retention device in such a way that the infusion cannulas and puncturing tips of the insertion head are set back relative to the contact face, to a second position, in which the infusion cannulas and puncturing tips of the insertion head protrude beyond the contact face to permit introduction of the infusion cannulas and puncturing tips into the body of the patient when the insertion movement is executed with the contact face of the insertion device placed on the body, wherein the housing has a first housing part, which carries the retention device and at least some of the at least one contact face, and a second housing part, which is movable relative to the first housing part from an operating position, in which the two housing parts are arranged in a position relative to one another that they adopt during the application of an insertion head with the insertion device, to a loading position, in which the retention device is accessible for correct engagement of the insertion head that is to be applied, wherein, after the insertion head has been engaged into the retention device, the second housing part can be moved back to the operating position, and the insertion device is designed in such a way that, after the insertion head has been engaged into the retention device and the second housing part has been moved back to the operating position, the insertion head is held with the retention device in the first position ready for application such that, at the start of the insertion movement the insertion head is separated from the retention device such that the insertion head executes at least the greatest part of the insertion movement free of the retention device.

3. The insertion device according to claim 2, wherein when the retention device is in the operating position, the insertion head is held by the retention device in the first position purely with a force fit, purely with a form fit, or with a combination of a force fit and form fit.

4. The insertion device according to claim 3, wherein when the retention device is in the loading position, the insertion head is held by the retention device purely with a form fit or with a combination of a force fit and form fit, said form fit cancelled during the movement of the second housing part from the loading position to the operating position.

5. The insertion device according to claim 3, wherein when the retention device is in the loading position, the insertion head is held by the retention device purely with a force fit, said force fit reduced during the movement of the second housing part from the loading position to the operating position.

6. The insertion device according to claim 2, wherein at least during most of the insertion movement or during the entire insertion movement of the insertion head, the retention device remains unmoved relative to the contact face.

7. The insertion device according to claim 6, wherein the retention device is immovable relative to those contact faces that are carried by the first housing part.

8. The insertion device according to claim 2, wherein the retention device is designed for holding the insertion head with a force-fit in the first position.

9. The insertion device according to claim 2, wherein the drive device comprises at least one pretensionable energy-storing element for providing the drive energy for the insertion movement, said energy-storing element being one of a helical spring, leg spring or leaf spring made of metal or plastic, a pneumatic compression spring, or a rubber spring element.

10. The insertion device according to claim 9, wherein the energy-storing element is pretensioned by the movement of the second housing part from the operating position to the loading position.

11. The insertion device according to claim 9, wherein the energy-storing element is pretensioned by the movement of the second housing part from the loading position to the operating position.

12. The insertion device according to claim 9, wherein, with the insertion head located in the first position, the energy-storing element is made ready in the pretensioned state, and the insertion movement is triggered by actuation of an actuation member, with increasing relaxation of the energy-storing element.

13. The insertion device according to claim 12, wherein the drive device comprises a thrust element for transmitting the drive energy to the insertion head to be applied and wherein, by displacing the thrust element counter to the direction of the insertion movement and subsequently locking it with a locking means that can be released by the actuation members, the energy-storing element is pretensioned and made ready in the pretensioned state.

14. The insertion device according to claim 2, wherein the second housing part can be pivoted relative to the first housing part for the movement from the operating position to the loading position.

15. The insertion device according to claim 2, wherein the second housing part is displaceable relative to the first housing part for the movement from the operating position to the loading position, the displacement being transverse to the direction of the insertion movement.

16. The insertion device according to claim 2, wherein the second housing part carries some of the contact faces.

17. The insertion device according to claim 2, wherein the insertion head can be engaged with the retention device by being pushed relative thereto in a direction transverse to the direction of the insertion movement.

18. The insertion device according to claim 2, the insertion device further comprising at least two actuation members, which have to be actuated simultaneously to trigger the insertion movement, a first of the actuation members being actuated by the contact face of the insertion device being pressed onto the body of the patient in the direction of the insertion movement of the insertion head.

19. The insertion device according to claim 18, wherein the first actuation member is one of a slide-shaped or button-shaped element which forms all the contact faces.

20. The insertion device according to claim 18, wherein a second actuation member is a button-shaped element which, when a user presses it with a finger tip, can be actuated in a direction transverse to the intended direction in which the insertion device is pressed onto the body of the patient.

21. The insertion device according to claim 18, wherein the at least two actuation members are operatively connected to one another such that by actuating one actuation member, a blocking of the other actuation member can be cancelled.

22. The insertion device according to claim 2, further comprising at least one actuation member for triggering the insertion movement, wherein the at least one actuation member can be actuated with one hand to permit one-handed triggering of the insertion movement.

23. The insertion device according to claim 2, further comprising at least one actuation member for triggering the insertion movement, wherein the at least one actuation member is designed such that, when an actuating force ceases, it automatically goes back to an unactuated state.

24. The insertion device according to claim 2, further comprising displacement means for effecting a transverse displacement of a displaceable actuation member of an insertion head to be held in the retention device, with at least one deployable infusion cannula and/or at least one deployable puncturing tip, during the movement of the second housing part from the loading position to the operating position, to permit automatic deployment of all the deployable infusion cannulas and puncturing tips of the insertion head during the movement of the second housing part from the loading position to the operating position.

25. The insertion device according to claim 24, wherein the displacement means for effecting a displacement of a displaceable actuation member comprises a run-on surface formed by the second housing part, by which an actuation member, displaceable transversely to the direction of the insertion movement, of an insertion head to be held in the retention device, with at least one deployable infusion cannula and/or at least one deployable puncturing tip, can be displaced during the movement of the second housing part from the loading position to the operating position, to ensure automatic deployment of all the deployable infusion cannulas and puncturing tips of the insertion head during the movement of the second housing part from the loading position to the operating position.

26. The insertion device according to claim 25, wherein the displacement means for effecting a displacement of a displaceable actuation member comprises a lever mechanism with which an actuation member, which is displaceable transverse to the direction of the insertion movement, of an insertion head to be held in the retention device, with at least one deployable infusion cannula and/or at least one deployable puncturing tip, can be displaced, during the movement of the second housing part from the loading position to the operating position, to ensure automatic deployment of all the deployable infusion cannulas and puncturing tips of the insertion head during the movement of the second housing part from the loading position to the operating position.

27. The insertion device according to claim 2, wherein the insertion device can be used several times to apply an insertion head.

28. The insertion device according to claim 2 and an insertion head which can be received in the insertion device and which comprises at least one infusion cannula and/or at least one puncturing tip.

29. The insertion head according to claim 28, wherein the insertion head comprises at least one deployable infusion cannula and/or at least one deployable puncturing tip, all the deployable infusion cannulas and puncturing tips of the insertion head being folded inwardly in the unactuated state, in which the insertion head, with the second housing part located in the loading position, is intended to be received in the retention device or is already received in the retention device, and the insertion device and the insertion head are designed such that all the deployable infusion cannulas and puncturing tips of the insertion head are automatically deployed during the movement of the second housing part from the loading position to the operating position.

30. The insertion device according to claim 2, wherein the insertion head is one of an infusion set, port and/or sensor arrangement and comprises at least one infusion cannula and/or at least one puncturing tip.

31. A method for applying an insertion head to the body of a patient, the insertion head comprising one of an infusion set, port and/or sensor arrangement and having at least one infusion cannula and/or at least one puncturing tip, said method involving using an insertion device comprising a housing having at least one contact face for placing the insertion device onto an application site on the body of the patient for application of the insertion head, a retention means with which the insertion head that is to be applied is temporarily held on the insertion device, and a drive means for effecting an insertion movement of the insertion head relative to the contact face, in the longitudinal direction of an infusion cannula or puncturing tip of the insertion head, from a first position, in which the insertion head is held ready for application by the retention means such that the infusion cannulas and puncturing tips are set back relative to the contact face, to a second position, in which the infusion cannulas and puncturing tips protrude substantially completely beyond the contact face, to permit introduction of the infusion cannulas and puncturing tips of the insertion head into the body of the patient when the insertion movement is executed with the contact face of the insertion device placed on the body, wherein the housing has a first housing part, which carries the retention means and at least some of the at least one contact face, and a second housing part, which is movable relative to the first housing part, from an operating position, in which the two housing parts are arranged in a position relative to one another that they adopt during the application of an insertion head, to a loading position, in which the retention device are accessible for engagement of the insertion head, wherein, after the insertion head has been engaged by the retention means, the second housing part can be moved back to the operating position, the insertion head then being held by the retention device ready for use, and wherein at the start of the insertion movement, the insertion head is separated from the retention means such that it executes the greatest part of the insertion movement free of the retention means, said method comprising the steps of:
 a) making ready the insertion device;
 b) moving the second housing part to the loading position;
 c) engaging the insertion head with the retention device such that the insertion head is held by the retention means;
 d) moving the second housing part from the loading position;
 e) arranging the insertion device with the contact face on the desired application site on the body of the patient such that the infusion cannulas and puncturing tips can penetrate correctly into the body during the insertion movement; and
 f) triggering the insertion movement, whereby the insertion head is separated from the retention means at the start of the insertion movement such that the insertion head executes at least the greatest part of the insertion movement free of the retention means.

32. The method according to claim 31, wherein the insertion head is held in the operating position by the retention means purely with a force fit, purely with a form fit, or with a combination of a force fit and form fit.

33. The method according to claim 32, wherein in the loading position the insertion head is held by the retention means purely with a form fit or with a combination of a force fit and form fit and the form fit is cancelled during the movement of the second housing part from the loading position to the operating position.

34. The method according to claim 32, wherein in the loading position the insertion head is held by the retention means purely with a force fit and the force fit is reduced during the movement of the second housing part from the loading position to the operating position.

35. The method according to claim 31, wherein the insertion device comprises a drive means comprising at least one pretensionable energy-storing element for providing the drive energy for the insertion movement, the energy-storing element being pretensioned by the movement of the second housing part from the operating position to the loading position and/or by the movement of the second housing part from the loading position to the operating position.

36. The method according to claim 31, wherein the second housing part is pivoted during the movement relative to the first housing part.

37. The method according to claim 31, wherein the insertion head is held in the retention means with a force fit, and the retention means is held immovably relative to the contact face during the insertion movement of the insertion head.

38. The method according to claim 31, wherein the insertion device further comprises a drive means having at least one pretensionable energy-storing element for providing the drive energy for the insertion movement, and the energy-storing element is made ready in the pretensioned state, and the insertion movement is then triggered by actuating an actuation member.

39. The method according to claim 38, wherein arranging the insertion device on the body of the patient and triggering the insertion movement is done with one hand.

40. The method according to claim 39, wherein the insertion head comprises at least one deployable infusion cannula and/or at least one deployable puncturing tip and, in a state in which all the deployable infusion cannulas and puncturing tips of the insertion head are folded inwardly is fitted into the retention means, all the deployable infusion cannulas and puncturing tips of the insertion head being deployed during the movement of the second housing part from the loading position to the operating position.

* * * * *

UNITED STATES PATENT AND TRADEMARK OFFICE
CERTIFICATE OF CORRECTION

| | | |
|---|---|---|
| PATENT NO. | : 7,771,393 B2 | Page 1 of 1 |
| APPLICATION NO. | : 12/047551 | |
| DATED | : August 10, 2010 | |
| INVENTOR(S) | : Jurg Liniger et al. | |

It is certified that error appears in the above-identified patent and that said Letters Patent is hereby corrected as shown below:

CLAIMS

| Column | Line | PTO | Should Read |
|---|---|---|---|
| 18 | 4 | in which the retention device | in which the retention means |
| 18 | 9 | retention device ready | retention means ready |
| 18 | 16 | with the retention device | with the retention means |

Signed and Sealed this

Thirtieth Day of November, 2010

David J. Kappos
*Director of the United States Patent and Trademark Office*